United States Patent
Gamard et al.

(10) Patent No.: US 11,344,695 B2
(45) Date of Patent: May 31, 2022

(54) GAS FLOW ARRESTOR

(71) Applicants: Stephan Christophe Fernand Gamard, Clarence, NY (US); Christopher Hugh Davies, Clarence, NY (US)

(72) Inventors: Stephan Christophe Fernand Gamard, Clarence, NY (US); Christopher Hugh Davies, Clarence, NY (US)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 663 days.

(21) Appl. No.: 16/298,205

(22) Filed: Mar. 11, 2019

(65) Prior Publication Data

US 2019/0344041 A1 Nov. 14, 2019

Related U.S. Application Data

(60) Provisional application No. 62/671,043, filed on May 14, 2018.

(51) Int. Cl.
*F16K 17/40* (2006.01)
*A61M 16/20* (2006.01)
(Continued)

(52) U.S. Cl.
CPC ...... *A61M 16/208* (2013.01); *A61M 16/0003* (2014.02); *A61M 16/06* (2013.01);
(Continued)

(58) Field of Classification Search
CPC ............ A61M 16/208; A61M 16/0003; A61M 16/0672; A61M 16/06; A61M 16/1005; A61M 16/20; A61M 16/0816; A61M 16/0087; A61M 2016/003; A61M 2202/0208; A61M 2205/584; A61M 2205/8281; F16K 17/383; F16K 37/0058;
(Continued)

(56) References Cited

U.S. PATENT DOCUMENTS

| 2,520,869 | A | * | 8/1950 | Windsor | ............... G01P 13/008 |
|-----------|---|---|--------|---------|---------------------------|
|           |   |   |        |         | 116/273                   |
| 2,970,561 | A | * | 2/1961 | Ashwood | ............ G01P 13/0013 |
|           |   |   |        |         | 116/273                   |

(Continued)

FOREIGN PATENT DOCUMENTS

WO 2008/068508 A1 6/2008

*Primary Examiner* — Minh Q Le
(74) *Attorney, Agent, or Firm* — Robert J. Hampsch

(57) ABSTRACT

A gas flow arrestor is provided that is configured to be coupled at one end to an oxygen concentrator, a VIPR type device associated with a compressed gas cylinder, or other gas delivery component such as a regulator or flowmeter and at the opposing end to a length of flexible tubing or hose that delivers the medical gas to the patient or patient breathing apparatus, such as a nasal cannula or breathing mask. The gas flow arrestor device includes a firebreak together with a visual flow indicator that is actuated by the flow of gas through the gas flow arrestor device. The visual flow indicator allows a user or patient to visually confirm from a distance whether or not gas is flowing to the patient or breathing apparatus.

21 Claims, 2 Drawing Sheets

(51) Int. Cl.
  *F17C 13/04* (2006.01)
  *A61M 16/06* (2006.01)
  *A61M 16/00* (2006.01)
  *F16K 17/38* (2006.01)
  *F16K 37/00* (2006.01)

(52) U.S. Cl.
  CPC ....... A61M 16/0672 (2014.02); F16K 17/383 (2013.01); F17C 13/04 (2013.01); *A61M 2016/003* (2013.01); *A61M 2202/0208* (2013.01); *F16K 37/0058* (2013.01); *F17C 2205/0323* (2013.01); *F17C 2270/025* (2013.01)

(58) Field of Classification Search
  CPC .............. F17C 13/04; F17C 2205/0323; F17C 2270/025
  USPC ..... 137/72, 553, 558; 116/273, 276; 251/82, 251/83
  See application file for complete search history.

(56) References Cited

U.S. PATENT DOCUMENTS

| | | | | |
|---|---|---|---|---|
| 3,119,369 A | * | 1/1964 | Harland | A47L 9/19 116/268 |
| 3,245,423 A | * | 4/1966 | Hansen | F16K 13/04 137/74 |
| 3,585,963 A | * | 6/1971 | Hiszpanski | G01P 13/008 116/206 |
| 4,280,523 A | * | 7/1981 | Norton | F16L 37/00 137/74 |
| 4,932,431 A | * | 6/1990 | Silagy | F16L 37/23 137/174 |
| 4,974,623 A | * | 12/1990 | Sturgis | F16K 17/40 137/74 |
| 5,027,845 A | * | 7/1991 | Silagy | F16L 37/23 137/74 |
| 5,103,757 A | * | 4/1992 | Palazzolo | G01F 15/12 116/276 |
| 5,542,445 A | * | 8/1996 | Adams | F16K 17/36 137/68.12 |
| 5,845,597 A | * | 12/1998 | Karpal | C02F 1/001 116/268 |
| 6,338,279 B1 | * | 1/2002 | Tsataros | G01F 1/28 340/607 |
| 6,386,196 B1 | | 5/2002 | Culton | |
| 7,004,168 B2 | * | 2/2006 | Mace | A61M 16/12 128/206.21 |
| 7,387,134 B2 | * | 6/2008 | Moore | F16K 17/383 137/74 |
| 8,602,048 B2 | | 12/2013 | Radford et al. | |
| 10,307,558 B2 | * | 6/2019 | Matusik | A61M 16/0683 |
| 2006/0266133 A1 | * | 11/2006 | Kim | G01F 1/22 73/865.5 |
| 2007/0221223 A1 | * | 9/2007 | McDermott | A61M 16/08 128/204.22 |
| 2008/0289695 A1 | * | 11/2008 | Holzer | F16K 17/383 137/73 |
| 2009/0288662 A1 | * | 11/2009 | Radford | A61M 16/0003 128/205.24 |
| 2009/0288663 A1 | | 11/2009 | East | |
| 2013/0019867 A1 | * | 1/2013 | Mashak | A61M 16/208 128/203.12 |
| 2013/0167952 A1 | * | 7/2013 | Mattson | F16K 37/0058 137/551 |
| 2015/0196723 A1 | | 7/2015 | Matusik | |
| 2018/0094730 A1 | | 4/2018 | Wojtach et al. | |
| 2018/0188094 A1 | * | 7/2018 | Matusik | A61M 16/0683 |
| 2020/0129713 A1 | * | 4/2020 | Matusik | A61M 16/0816 |

* cited by examiner

GAS FLOW ARRESTOR

CROSS REFERENCE TO RELATED APPLICATIONS

The present application claims priority from U.S. Provisional Patent Application Ser. No. 62/671,043 filed on May 14, 2018, the disclosure of which is incorporated by reference herein.

TECHNICAL FIELD

The present invention relates to gas flow arrestor devices for medical gas applications, and more particularly to a gas flow arrestor device configured to be coupled at one end to an oxygen concentrator, a VIPR device associated with a compressed gas cylinder or other medical gas delivery component and at the opposing end to a length of flexible tubing or hose that delivers the medical gas to the patient or patient breathing apparatus, such as a nasal cannula or breathing mask.

BACKGROUND

Medical gases such as medical oxygen used for respiratory assistance in a patient is typically provided from an oxygen concentrator or a compressed gas cylinder having a valve integrated pressure regulator (VIPR). The VIPR device coupled to the compressed gas cylinder is configured to meter out precise gas flows based on pre-set flow selection knobs that are often disposed on or associated with the VIPR device. Oxygen containing gas from within the cylinder flows via the VIPR to a hose which that delivers the required oxygen gas to the patient via a breathing attachment such as a cannula or mask.

Several distinct problems have been identified with the prior art medical oxygen cylinders having VIPR devices integrated therewith. For example, the typical tubing/hose as well as patient breathing apparatus or accessories such as the cannula or mask are often made of a plastic or other flammable material. In the case of a fire that is initiated at or near the patient such as by means of a lit cigarette or lighter, the flame can propagate along the plastic breathing apparatus and hose back to the compressed gas cylinder or oxygen source potentially leading to more severe safety incidents. Prior art attempts to address this problem have produced flame arrestors or firebreaks that are inserted into the hose or otherwise along the oxygen flow delivery path between the VIPR and the patient. Examples of commercially available flame arrestors or firebreaks include those shown and described in U.S. Patent Application Publication No. 2009/0288663, the disclosure of which is incorporated by reference herein.

Additional problems associated with compressed gas cylinders configured to deliver medical oxygen via a VIPR device relate to oxygen flow indication. For example, when a user or patient turns the pre-set flow selection knobs on the VIPR device, there is often no visual indication that oxygen gas is actually flowing out from the compressed gas cylinder or if it is flowing, the oxygen is flowing at the proper flow rate. Also, when the breathing apparatus such as the cannula or mask is decoupled from the oxygen source, the oxygen will continue to flow until the user turns the flow selection knob back to zero or closed position. Failure of the user to close the compressed gas cylinder by turning the flow selection knob back to zero flow or a 'closed' position, could lead to accidental oxygen discharge and potentially serious safety hazards resulting from the user error. Again, however, there is typically no visual indication to such user that oxygen is not flowing out from the compressed gas cylinder after such disconnection. Prior art visual indicators include conventional 'ball-style' flow meters. Such conventional flow meters are often rather large compared to the flexible tubing or hose to which it is attached and often require precise orientations to operate effectively. In addition, connection of a conventional flow meter device between the VIPR device and the patient breathing apparatus introduces another point of failure or disruption in the breathing circuit.

What is needed is an improved gas flow arrestor device that combines the features and functionality of firebreaks and visual flow indication. Preferably, such a device should be compact and capable of placement anywhere along a patient breathing circuit to facilitate safe delivery of a medical gas to a patient.

SUMMARY OF THE INVENTION

The present invention may be characterized as a gas flow arrestor device comprising: (i) a main body section defining a first proximal end and having an inlet configured to receive a flow of a gas from a valve integrated pressure regulator (VIPR) associated with a compressed gas cylinder or an oxygen concentrator; (ii) a forward body section defining a distal end and having an outlet configured to deliver the flow of the gas to a patient or a breathing apparatus, such as a nasal cannula or breathing mask; (iii) an internal flow path fluidically coupling the inlet to the outlet; (iv) a sealing member disposed in the internal flow path and configured to allow the gas to flow from the inlet to the outlet when the gas flow arrestor device is in an open position and to prevent the gas to flow from the inlet to the outlet when the gas flow arrestor device is in a closed position; (v) a spring configured for biasing the sealing member within the internal flow path; (vi) a firebreak having a fusible stop disposed along the internal flow path, the firebreak configured to move the sealing member such that the gas flow arrestor device is in the closed position upon fusing of the stop; and (vii) a visual flow indicator that is actuated by the flow of gas along the internal flow path from the inlet to the outlet, the visual flow indicator configured to have a first display when the gas is not flowing along the internal flow path from the inlet to the outlet and at least a second display, different from the first display, when the gas is flowing along the internal flow path from the inlet to the outlet. The fusible stop is preferably made of a plastic material that has a melting point less than that of the material of the main body section, the forward body section, and the flexible tube or hose connected to the forward body section.

The first display, preferably red in color, and the second display, preferably green in color, are visually detectable through a window on the main body section of the gas flow arrestor device and can be seen by the patient and/or user from a location apart from or away from the gas flow arrestor device. The forward body section of the present gas flow arrestor device is preferably a tapered or barbed fitting configured to attach to a hose or tube and suitable for delivery of medical oxygen gas to a patient. The visual flow indicator may also optionally include gas flow metering indicia in analog or digital form that identifies an estimate of the flow rate of the gas through the gas flow arrestor device.

In some embodiments, the default position of the gas flow arrestor device is in the closed positioned where the sealing mechanism is engaged such that it prevents gas flow through the gas flow arrestor device. Other embodiments of the gas flow arrestor device are configured to be initially positioned in the open position where the sealing mechanism is apart from the seat such that it allows gas flow through the gas flow arrestor device until such time as the fusible stop on the firebreak melts or is otherwise removed.

An additional feature that may be designed or incorporated into the gas flow arrestor device is a hose coupling detection mechanism. In such embodiments, the gas flow arrestor device is configured to be in the closed position as a default position and gas flow arrestor device moves to the open position only when the distal end and outlet are connected via the hose or tube to the patient or the breathing apparatus. The gas flow arrestor device moves back to closed position upon removal of the flexible tube or hose from the distal end and outlet or upon removal or melting of the fusible stop.

BRIEF DESCRIPTION OF THE DRAWINGS

While the present invention concludes with claims distinctly pointing out the subject matter that Applicant regards as his invention, it is believed that the invention will be better understood when taken in connection with the accompanying drawings in which:

DETAILED DESCRIPTION

The presently disclosed gas flow arrestor device includes a conventional firebreak that is configured to shut or stops the flow of gas in the presence of a fire or flame proximate the firebreak and a visual flow indicator that is actuated by the flow of gas through the gas flow arrestor device. The visual flow indicator allows a user or patient to visually confirm from a distance whether or not gas is flowing to the patient or breathing apparatus. Optionally, the gas flow arrestor device may also include a coupling detection mechanism that prevents flow of the gas through the device unless the flexible tubing or hose is coupled to the outlet of the flow arrestor device. Details of select embodiments of the present gas flow arrestor device are provided in the paragraphs that follow.

Turning now to the drawings, there is shown a partial cross section view of an embodiment of the gas flow arrestor device 10 configured to be coupled at one end to a concentrator, a VIPR device associated with a compressed gas cylinder, or other gas delivery component such as a flowmeter or regulator, and at the opposing end to a length of flexible tubing or hose 80 that delivers the gas to the patient or patient breathing apparatus, such as a nasal cannula or breathing mask.

Figure 1:
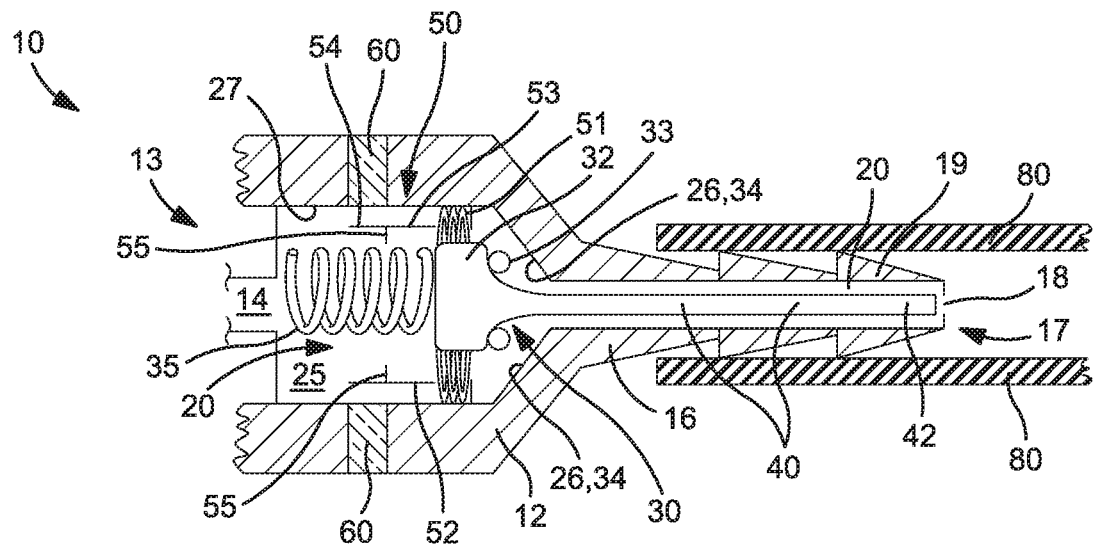
FIG. 1 is a cross section view of a gas flow arrestor device shown in the open position in accordance with an embodiment of the present invention.

In one embodiment of the present gas flow arrestor device shown in FIG. 1, the flow arrestor device 10 includes a main body section 12 defining a first proximal end 13 and an inlet 14; a forward body section 16 defining a distal end 17 and an outlet 18; and an internal flow path 20 with a cavity 25 connecting the inlet 14 to the outlet 18. In the illustrated embodiments, the forward body section 16 is shown as a tapered or barbed fitting 19 suitable to be inserted into the hose or tube 80 via an interference fit. The proximal end 13 of the main body section 12 is configured to be connected to a gas source, such as a compressed oxygen cylinder or oxygen concentrator or other gas delivery component. Such connection may be by flexible hose or tubing or may be a direct connection to a VIPR device on a compressed gas cylinder. Such direct connections may be by a quick connect a threaded connection or other suitable connectors.

A sealing member 30 and spring 35 are disposed within the cavity 25. As seen in the drawings, the sealing member 30 includes a piston assembly 32 that is configured to laterally move within the cavity 25 along the internal flow path 20 and an O-ring 33 disposed to engage a seat 34 so as to seal off the gas flow along the internal flow path 20.

The position of sealing member 30 within the cavity 25 and internal flow path 20 defines whether the flow arrestor device 10 is in an open position or a closed position. In the closed position, the piston assembly 32 and the O-ring 33 are in sealing contact against an interior wall 26 of the main body section 12 sealing off the flow of gas within the cavity 25 towards the outlet 18. In the open position the piston assembly 32 and O-ring 33 are spaced away from the interior wall 26 of the cavity 25 in the main body section 12 allowing a flow of gas from the inlet 14 through the cavity 25 and to the outlet 18. In FIG. 1, the spring 35 is shown biasing the sealing member 30 within the internal flow path towards the closed position. However, the flow arrestor device 10 is shown in the open position when the gas is not flowing along the internal flow path 20 from inlet 14 to outlet 18 due to the length of a firebreak 40 abutting against the distal end 17 of the flow arrestor device 10.

The flow arrestor device 10 also includes a firebreak 40 having a fusible stop 42 disposed along the internal flow path 20. The fusible stop 42 is preferably made of a plastic material having a melting point less than that of the material of the main body section 12, the forward body section 16, and the flexible tubing or hose 80 that typically gets connected to the distal end 17 of the flow arrestor device 10. When the fusible stop 42 melts or is otherwise deformed such as in the case of a fire or flame, the sealing member 30 moves and flow arrestor device 10 shifts to the closed position shutting the flow of gas and possible minimizing the severity of the event. The spring 35, O-ring 33, and piston assembly 32 are also at the heart of the fire arrestor or 'firebreak' concept. Upon melting or deforming of the fusible stop 42, the spring 35 pushes the piston assembly 32 and O-ring 33 into sealing engagement against seat 34 on an inside wall 26 of the cavity 25 and seals or closes the gas flow path through the flow arrestor device 10.

The flow arrestor device 10 further includes a visual flow indicator 50 that is actuated by the flow of gas along the internal flow path 20 from the inlet 14 to the outlet 18. The visual flow indicator 50 allows a user to visually confirm from a distance whether or not gas is flowing through the device at any point in time. In the preferred embodiments, the visual flow indicator 50 includes a first display 53, preferably red in color, indicating that gas is not flowing along the internal flow path 20 from the inlet 14 to the outlet 18 and at least a second display 54, different from the first display and preferably green in color indicating that the gas is flowing along the internal flow path 20 from the inlet 14 to the outlet 18.

In the present embodiments the visual flow indicator 50 is also disposed within the cavity 35 and is shown in the illustrated embodiments as a spring 51 and a slider 52. The slider 52 has an exterior surface disposed at or near the peripheral edge 27 of the cavity 25. The exterior surface of the slider 52 may be partitioned into a first section (i.e. first display 53) and a second section (i.e. second display 54). The slider 52 also has a shoulder extension 55 extending radially inward away from the peripheral edge 27 of the cavity 25. The present flow arrestor device 10 further includes a window 60 disposed in the main body section 12 at a location near or adjacent to the slider 52 to allow a visual indication of the slider through the window 60, and more particularly either the first section (i.e. first display 53) through the window or the and a second section (i.e. second display 54) through the window.

Preferably, the slider 52 includes a first section and a second section that is visibly differentiated from the first section. Preferably, the first section (i.e. first display 53) may be colored green while the second section (i.e. second display 54) may be colored red. When gas flows from the gas source through the inlet 14 into the cavity 25 of the internal flow path 20, the gas flow will exert a force on the shoulder extension 55 which moves the slider 52 such that the second section or second display 54 of the slider 52 is visible through the window 60. In this manner, when the flow arrestor device 10 is in the open position and gas is flowing from inlet 14 through the cavity 25 to outlet 18 at a positive pressure, the gas flow moves the slider 52 such that the second section (i.e. second display 54), preferably green in color, is visible through the window 60. Conversely, when the flow arrestor device 10 is in the closed position or in the open position with no gas flowing from the inlet 14 through the cavity 25 to the outlet 18, spring 51 acts on or moves the slider 52 such that the first section (i.e. first display 53), preferably red in color, is visible through the window 60. Such arrangement will display a green visual indicator that a gas flow exists and a red visual indicator when no gas flow is happening.

In some contemplated embodiments, the window 60 and/or slider 52 may also include markings that allows visual indication not only of the whether the flow arrestor device 10 is in the open position with a flow of gas from the inlet 14 through the cavity 25 to the outlet 18, but also the magnitude of the flow, preferably indicating the estimated flow rate of the gas flowing from the inlet 14 through the cavity 25 to the outlet 18 as different gas flow rates would move the slider 52 to a different position relative to the window 60. By using various markings or color gradations on the window 60 and/or slider 52 more information regarding the gas flow may be visually available to the user.

Figure 2:
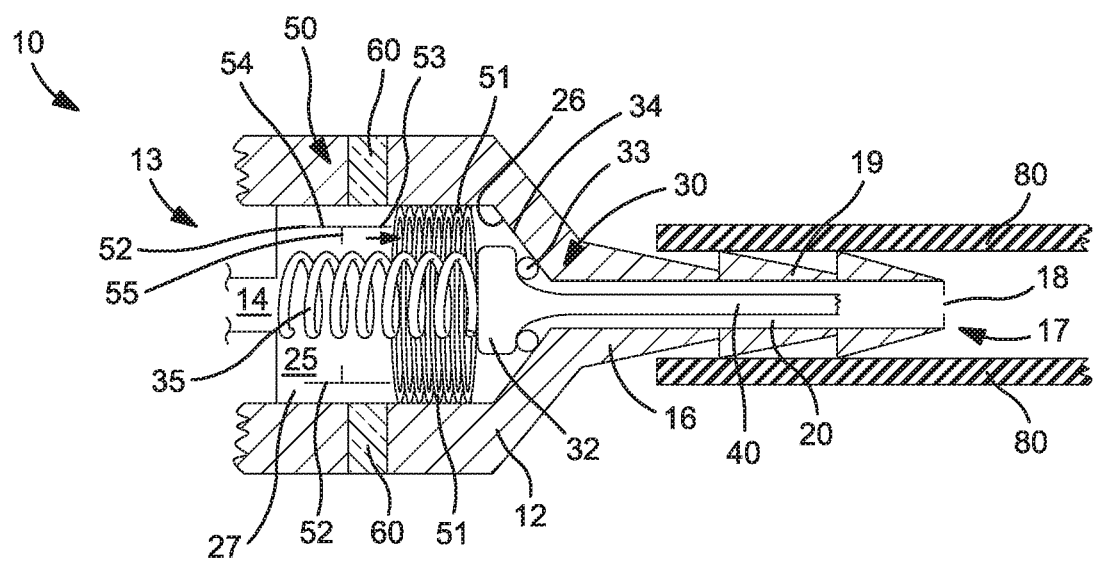
FIG. 2 is a cross section view of a gas flow arrestor device of FIG. 1 shown in the closed position.
Figure 3:
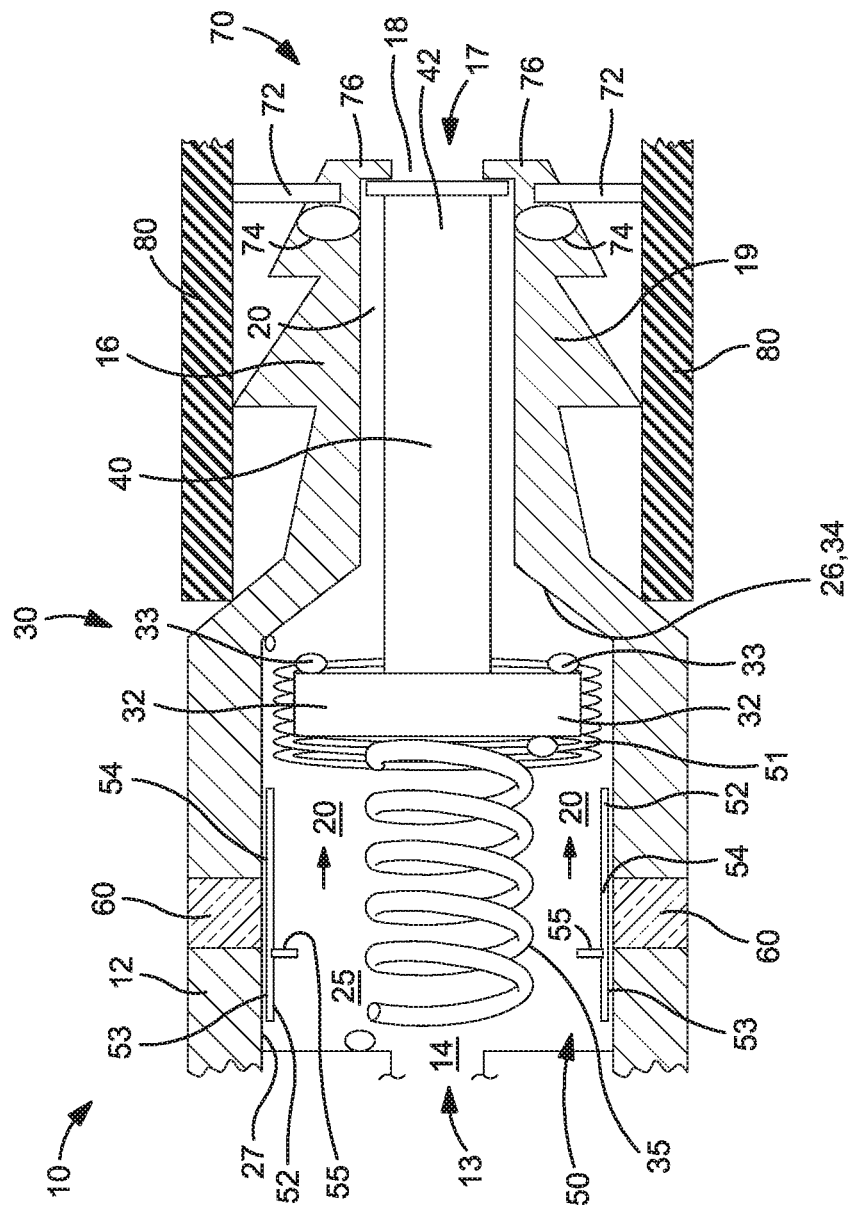
FIG. 3 is a cross section view of a gas flow arrestor device shown in the open position in accordance with another embodiment of the present invention.

Turning now to the embodiment of the flow arrestor device 10 shown in FIG. 3, it is in many respects similar to the embodiment shown in FIGS. 1 and 2 and the functionality of the firebreak and visual flow indicators will not be repeated. A key difference in the flow arrestor device of FIG. 3 is that the flow arrestor device 10 starts in the closed position and shifts to the open position only after the flow arrestor device 10 is connected to the flexible tubing or hose 80 as determined by a coupling detection mechanism 70. The flow arrestor device 10 shifts back to the closed position either when the flexible tubing or hose 80 is removed from the distal end 17 of the forward body section 16 or when the fusible stop 42 of the firebreak 40 melts or is otherwise deformed as in the presence of a fire.

Specifically, FIG. 3 shows the embodiment of the present flow arrestor device 10 in an open position connected to the gas source or VIPR device at one end and to the flexible tubing or hose 80 at the other end. As indicated above, an added feature to this embodiment compared to the embodiment of FIGS. 1 and 2 is the coupling detection mechanism 70 that comprises a coupling pin 72, a pivot 74 and a retention shoulder 76 all disposed near the distal end 17 of the forward body section 16.

In this embodiment, when the flexible tubing or hose 80 is coupled to the distal end 17 of the forward body section 16, the sealing member 30 (e.g. piston assembly 32 and O-ring 33) is moved or displaced towards the inlet 14 causing the flow arrestor device 10 to shift from the closed position to the open position. Such displacement is accomplished in the illustrated embodiment by means of the coupling pin 72, retention shoulder 76, and pivot 74. More specifically, when the flexible tubing or hose 80 is coupled to the distal end 17 of the forward body section 17, the inner surface of the hose or tube pushes the coupling pin 72 inward which in turn rotates the retention shoulder 76 via the pivot 74 into a position that moves the firebreak 40 in the direction towards the inlet 14 and placing the flow arrestor device 10 in the open position. The retention shoulder 76 preferably locks or restrains the firebreak 40 in place but allows gas flow through the outlet 18. As the firebreak 40 is pushed back, the sealing member 30 (e.g. piston assembly 32 and O-ring 33) separates or moves away from the seat 34 allowing gas to flow from the VIPR device through the cavity 25 of the main body section 12 and out through the outlet 18 in the forward body section 17 to the hose or tube 80 and then on to the patient breathing apparatus.

Conversely, when the hose or tube 80 is removed from forward body section 17 of the flow arrestor device 10, the coupling pin 72 and retention shoulder 76 recede so as to no longer restrain the firebreak 40. Without such restraint, the flow arrestor device 10 will return to the closed position where the spring 35 forces the sealing member 30 towards the outlet 18 until the O-ring 33 presses against the seat 34 which seals off the flow of the gas from the inlet 14 to the outlet 18.

Although the gas flow arrestor device has been discussed with reference to one or more preferred embodiments, numerous changes and omissions can be made without departing from the spirit and scope of the present invention as set forth in the appended claims.

What is claimed is:

1. A gas flow arrestor device comprising:
   a main body section defining a first proximal end and having an inlet configured to receive a flow of a gas from a compressed gas cylinder;
   a forward body section defining a distal end and having an outlet configured to deliver the flow of the gas to a patient or a breathing apparatus;
   an internal flow path fluidically coupling the inlet to the outlet;
   a sealing member disposed in the internal flow path and configured to allow the gas to flow from the inlet to the outlet when the gas flow arrestor device is in an open position and to prevent the gas to flow from the inlet to the outlet when the gas flow arrestor device is in a closed position;
   a spring configured for biasing the sealing member within the internal flow path;
   a firebreak having a fusible stop disposed along the internal flow path, the firebreak configured to move the sealing member such that the gas flow arrestor device is in the closed position upon fusing of the stop; and
   a visual flow indicator that is actuated by the flow of gas along the internal flow path from the inlet to the outlet, the visual flow indicator disposed in the main body section and configured to have a first colored display when the gas is not flowing along the internal flow path from the inlet to the outlet and a second colored display, different than the first colored display, when the gas is flowing along the internal flow path from the inlet to the outlet;

wherein the first colored display and the second colored display are visually detectable from a location away from the gas flow arrestor device and wherein the first colored display is different than the second colored display and the color of the first colored display is different than the color of the second colored display.

2. The gas flow arrestor device of claim 1 wherein the sealing member is biased by the spring such that the gas flow arrestor device is in the open position and sealing member moves such that the gas flow arrestor device is in the closed position upon removal or fusing of the stop.

3. The gas flow arrestor device of claim 1 wherein the forward body section is a tapered or barbed fitting configured to attach to a hose or tube.

4. The gas flow arrestor device of claim 3 wherein the sealing member is biased by the spring such that the gas flow arrestor device is in the closed position and sealing member moves such that the gas flow arrestor device is in the open position when the distal end and outlet are connected via the hose or tube to the patient or the breathing apparatus and the sealing member moves such that the gas flow arrestor device is in the closed position upon removal of the hose or tube connecting the distal end and outlet to the patient or the breathing apparatus removal or the sealing member moves such that the gas flow arrestor device is in the closed position upon fusing of the stop.

5. The gas flow arrestor device of claim 1 wherein the gas is oxygen.

6. The gas flow arrestor device of claim 1 wherein the visual flow indicator further comprises a gas flow metering indicia in analog or digital form that identifies an estimate of the flow rate of the gas along the internal flow path from the inlet to the outlet.

7. The gas flow arrestor device of claim 1 wherein the first colored display is red in color and second colored display is green in color.

8. The gas flow arrestor device of claim 1 wherein the visual flow indicator is a slider disposed within a cavity in the main body section and configured to move laterally within the cavity when gas is flowing through the internal flow path, and wherein the first colored display is a first section of the slider and the second colored display is a second section of the slider.

9. The gas flow arrestor device of claim 8 wherein the slider is visually detectable via a window on an exterior surface of the main body section, wherein the slider is configured to traverse the window.

10. The gas flow arrestor device of claim 1 wherein the visual flow indicator is visually detectable through a window disposed on an exterior surface of the main body section.

11. The gas flow arrestor device of claim 1 wherein the visual flow indicator is visually detectable through a window disposed radially around the main body section.

12. The gas flow arrestor device of claim 1 further comprising a second spring configured for biasing the visual flow indicator to a first position that shows the first colored display through a window on the main body section and wherein the visual flow indicator moves to a second position to show the second colored display through the window on the main body section when the visual flow indicator is actuated by the gas flowing along the internal flow path from the inlet to the outlet.

13. The gas flow arrestor device of claim 1 wherein the main body section is a tapered or barbed fitting configured to be connected to a hose or tube.

14. The gas flow arrestor device of claim 1 wherein the main body section is configured to be directly connected to a fitting on the compressed gas cylinder.

15. The gas flow arrestor device of claim 14 wherein the main body section is configured to be directly connected to the fitting via screw threads.

16. The gas flow arrestor device of claim 1 wherein the main body section is configured to be directly connected to a valve integrated pressure regulator (VIPR) device coupled to the compressed gas cylinder.

17. The gas flow arrestor device of claim 1 wherein the internal flow path has an internal surface that acts as a seat for the sealing member when the gas flow arrestor device is in the closed position.

18. The gas flow arrestor device of claim 1 wherein the fusible stop is of a plastics material having a melting point less than that of the material of the main body section and forward body section.

19. The gas flow arrestor device of claim 3 wherein the fusible stop is of a plastic material having a melting point less than that of the material of the hose or tube.

20. The gas flow arrestor device of claim 1 wherein the breathing apparatus is a nasal cannula.

21. The gas flow arrestor device of claim 1 wherein the breathing apparatus is a breathing mask.

\* \* \* \* \*